(12) United States Patent
Daniel et al.

(10) Patent No.: US 11,497,608 B2
(45) Date of Patent: *Nov. 15, 2022

(54) BENDABLE GRAFT CONTAINMENT CAGE

(71) Applicant: DePuy Synthes Products, Inc., Raynham, MA (US)

(72) Inventors: Steffan Daniel, Zuchwil (CH); André Furrer, Zuchwil (CH)

(73) Assignee: DEPUY SYNTHES PRODUCTS, INC., Raynham, MA (US)

(*) Notice: Subject to any disclaimer, the term of this patent is extended or adjusted under 35 U.S.C. 154(b) by 221 days.

This patent is subject to a terminal disclaimer.

(21) Appl. No.: 15/886,757

(22) Filed: Feb. 1, 2018

(65) Prior Publication Data

US 2018/0221153 A1 Aug. 9, 2018

Related U.S. Application Data

(60) Provisional application No. 62/455,345, filed on Feb. 6, 2017, provisional application No. 62/455,370, filed on Feb. 6, 2017.

(51) Int. Cl.
*A61F 2/28* (2006.01)
*A61F 2/30* (2006.01)

(52) U.S. Cl.
CPC ............ *A61F 2/2846* (2013.01); *A61F 2/28* (2013.01); *A61F 2/2803* (2013.01);
(Continued)

(58) Field of Classification Search
CPC ............ A61F 2002/285; A61F 2/2846; A61F 2/2803; A61F 2/3099; A61F 2/28;
(Continued)

(56) References Cited

U.S. PATENT DOCUMENTS 5,554,194 A 9/1996 Sanders
5,730,743 A 3/1998 Kirsch et al.
(Continued)

FOREIGN PATENT DOCUMENTS

CN 103298429 A 9/2013
CN 103826573 A 5/2014
(Continued)

OTHER PUBLICATIONS

J Oral Maxillofac Res 2017 (Apr.-Jun.): vol. 8, No. 2, e1, p. 1-12 (Year: 2017).*

*Primary Examiner* — Jennifer Dieterle
*Assistant Examiner* — Rebecca Lynee Zimmerman
(74) *Attorney, Agent, or Firm* — Fay Kaplun & Marcin, LLP

(57) ABSTRACT

A bone graft containment device includes a plurality of cage segments connected to one another along a longitudinal axis, each of the cage segments connected to an adjacent one of the cage segments via a connection which permits movement of the cage segments relative to one another so that the bone graft containment device is deformable to a desired configuration for placement within a target space of a bone, each cage segment extending along from a first end to a second end and including a channel extending therethrough so that channels of the plurality of cage segments, in an initial configuration, are aligned along the longitudinal axis, the channels configured to be packed with a bone graft material.

20 Claims, 8 Drawing Sheets

(52) U.S. Cl.
CPC . *A61F 2002/285* (2013.01); *A61F 2002/2835* (2013.01); *A61F 2002/30329* (2013.01); *A61F 2002/30518* (2013.01); *A61F 2310/00005* (2013.01)

(58) Field of Classification Search
CPC .... A61F 2002/30329; A61F 2002/2835; A61F 2002/30518; A61C 8/0006; A61C 8/0027; A61B 17/8071
See application file for complete search history.

(56) References Cited

U.S. PATENT DOCUMENTS

| | | | |
|---|---|---|---|
| 6,391,059 B1 | 5/2002 | Lemperle et al. | |
| 8,840,614 B2 * | 9/2014 | Mikhail | A61F 2/2803 606/86 R |
| 9,144,506 B2 | 9/2015 | Phelps | |
| 9,554,877 B2 | 1/2017 | Bassett et al. | |
| 2002/0062127 A1 | 5/2002 | Schumacher et al. | |
| 2002/0107571 A1 | 8/2002 | Foley | |
| 2003/0083746 A1 | 5/2003 | Kuslich | |
| 2004/0167625 A1 | 8/2004 | Beyar et al. | |
| 2005/0234557 A1 | 10/2005 | Lambrecht et al. | |
| 2005/0273165 A1 * | 12/2005 | Griffiths | A61C 8/0006 623/16.11 |
| 2010/0010633 A1 | 1/2010 | Kohm | |
| 2010/0161074 A1 * | 6/2010 | McKay | A61L 24/046 623/23.5 |
| 2011/0098760 A1 | 4/2011 | Griffiths et al. | |
| 2012/0296441 A1 | 11/2012 | Mikhail et al. | |
| 2015/0045895 A1 * | 2/2015 | Laurence | A61F 2/4425 623/17.16 |
| 2016/0287391 A1 | 10/2016 | Larsen et al. | |
| 2017/0354503 A1 | 12/2017 | Larsen et al. | |
| 2018/0116802 A1 | 5/2018 | Daniel et al. | |
| 2018/0193530 A1 | 7/2018 | Barbas et al. | |

FOREIGN PATENT DOCUMENTS

| | | |
|---|---|---|
| CN | 204501109 U | 7/2015 |
| CN | 105147374 A | 12/2015 |
| EP | 1 755 496 | 2/2007 |
| EP | 2 730 255 | 5/2014 |
| JP | 2008501435 | 1/2008 |
| JP | 2016105828 | 6/2016 |
| WO | 2012/068062 | 5/2012 |
| WO | 2014/125381 | 8/2014 |

* cited by examiner

# BENDABLE GRAFT CONTAINMENT CAGE

PRIORITY CLAIM

The present application claims priority to U.S. Provisional Patent Application Ser. No. 62/455,370 and U.S. Provisional Patent Application Ser. No. 62/455,345 both of which were filed on Feb. 6, 2017 and the entire disclosures of which are expressly incorporated herein by reference.

BACKGROUND

Mandible defects are often treated with bone grafts and/or implants such as, bone plates, to assist with healing. The bone grafts may be placed in the target area using any of a variety of methods. However, without a container for the bone graft, the graft may fall away from a target site before it can be incorporated by the body into the healing bone.

SUMMARY

The present invention is directed to a bone graft containment device, comprising a plurality of cage segments connected to one another along a longitudinal axis, each of the cage segments connected to an adjacent one of the cage segments via a connection which permits movement of the cage segments relative to one another so that the bone graft containment device is deformable to a desired configuration for placement within a target space of a bone, each cage segment extending along from a first end to a second end and including a channel extending therethrough so that channels of the plurality of cage segments, in an initial configuration, are aligned along the longitudinal axis, the channels configured to be packed with a bone graft material.

The present invention is also directed to a bone graft containment device, comprising a first cage segment extending from a first end to a second end and including a first channel extending therethrough, a second cage segment extending from a first end to a second end and including a second channel extending therethrough, the first end of the second cage segment connected to the second end of the first cage segment so that, when in an initial configuration, the first and second channels are aligned along a longitudinal axis, the first and second cage segments movable relative to one another to a desired configuration for placement in a target space of a bone, the first and second channels configured to be packed with a bone graft material, and a first slot extending between the first and second cage segments to define a space therebetween.

The present invention is also directed to a method for treating a bone, comprising moving cage segments of a graft containment device relative to one another from an initial configuration to a desired connection, the cage segments connected to one another along a longitudinal axis in the initial configuration, packing a graft material within channels of the cage segments, the channels aligned along the longitudinal axis in the initial configuration, placing the graft containment device in a target space of a bone, and fixing the graft containment device to the bone via a fixation element.

The present invention is also directed to a bone graft containment device, comprising a body extending longitudinally from a first end to a second end and including a channel extending longitudinally therethrough and a plurality of slots extending laterally into the body in communication with the channel to define a plurality of cage segments, the slots extending along a first side of the body so that a second side of the body opposite the first side includes a continuous surface, the body movable between a substantially straight configuration and a curved configuration in which cage segments are moved relative to one another to reduce a size of the slots therebetween.

The present invention is also directed to a method for treating a bone, comprising packing a graft material into a channel of a graft containment device, the graft containment device including a mesh body extending longitudinally from a first end to a second end and including the channel extending longitudinally therethrough, a plurality of slots extending laterally into a first side of the mesh body in communication with the channel to define a plurality of cage segments so that a second side of the mesh body opposite the first side includes a continuous surface, bending the graft containment device relative to a longitudinal axis of the graft by drawing edges of adjacent cage segments toward one another, positioning the graft containment device in a target space of a bone, and fixing the graft containment device to the bone via a bone fixation element.

BRIEF DESCRIPTION

DETAILED DESCRIPTION

Figure 1:
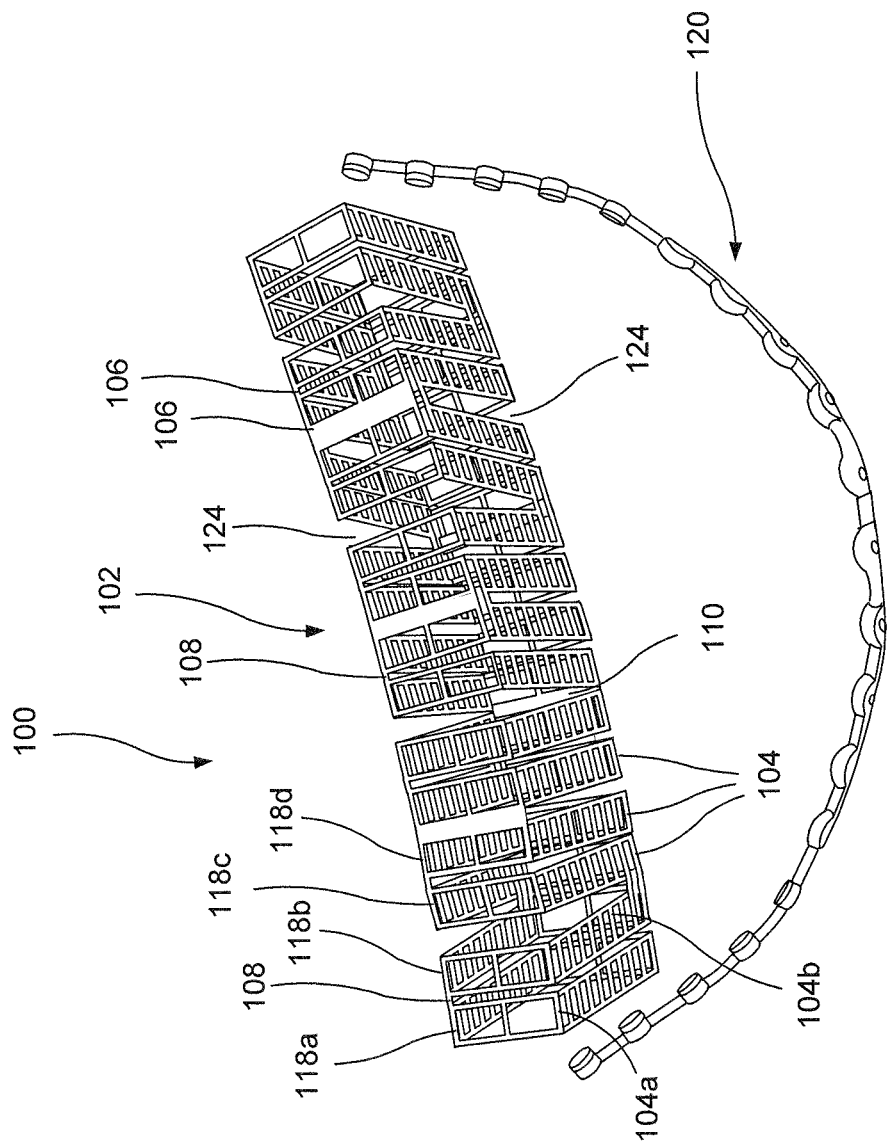
FIG. 1 shows a perspective view of a system according to an exemplary embodiment of the present disclosure, in an initial configuration.

The present invention may be understood with reference to the following description and the appended drawings, wherein like elements are referred to with the same reference numerals. The present invention relates to the treatment of bone and, in particular, relates to treatments using bone grafts and bone graft substitutes. Exemplary embodiments of the present invention describe a graft containment cage configured to be positioned in a gap or space in a target bone (e.g., the mandible) so that graft material may be packed therein to encourage and guide the generation of new bone in the gap/space. In one exemplary embodiment, the cage may be positioned between two separated portions of bone to generate new bone joining the separated portions of bone. It will be understood by those of skill in the art, however, that the graft containment cage may be inserted or positioned within any gap or space of the target bone including, for example, at an end of the bone, so that there is bone only on one side of the graft containment cage, or within a recessed space of the bone, so that three sides of the graft containment cage contact bone. Exemplary embodiments of the graft containment device comprise a plurality of cage segments connected to one another at various connection points such that the cage segments are movable relative to one another to bend and/or extend the graft containment device, as desired, to fill the gap or space in the target bone. Although the exemplary embodiment is shown and described in regard to the treatment of a mandible, it will be understood by those of skill in the art that the graft containment device of the present invention may also be formed in different shapes and sized to permit use in treating other types of bone which would benefit from the use of a graft containment device.

Figure 2:
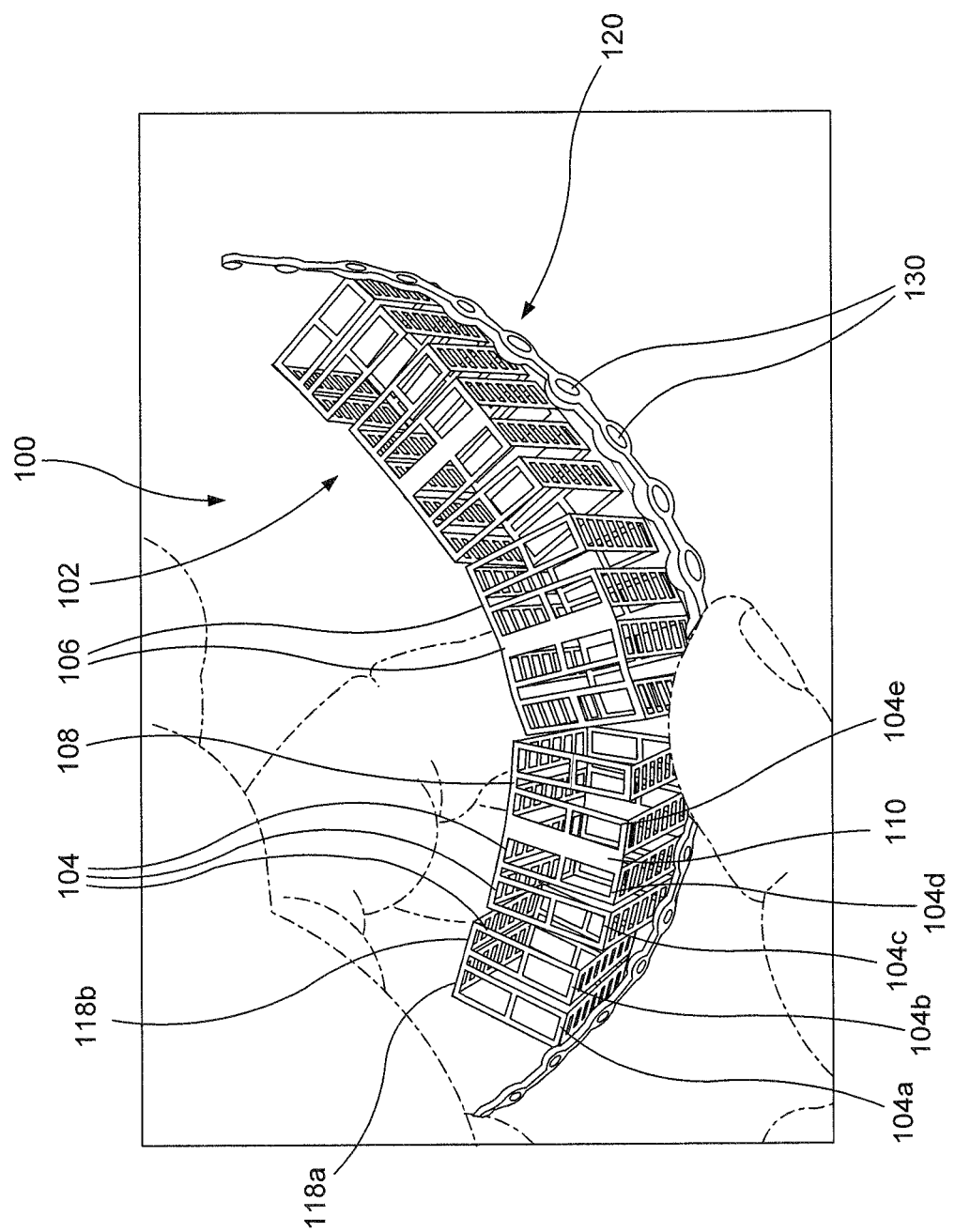
FIG. 2 shows a perspective view of the system of FIG. 1, in an adjusted configuration.

As shown in FIGS. 1-5, a system 100 according to an exemplary embodiment of the present disclosure comprises a bone graft containment device 102 including a plurality of cage segments 104 connected to one another at specific connection points 106 via, for example, one of a first connection 108 and a second connection 110. A location, position and/or type of the connection points 106 (e.g., whether the connection point 106 includes the first connection 108 or the second connection 110) allows the graft containment device 102 to be bent and/or expanded so that the graft containment device 102 may be positioned as desired within a target gap or space of a bone (e.g., to replace a missing, damaged or diseased portion of a mandible). The graft containment device 102 may be sized and shaped so that, when the graft containment device 102 is positioned in the target gap or space, cage segments 104 at ends of the graft containment device 102 substantially match an outer profile of a target portion of bone which formerly occupied the space to occupied by the device 102. In one exemplary embodiment, the graft containment device 102 is sized and shaped to be positioned between two separated portions of a target bone. The connection points 106 permit the graft containment device 102 to be longitudinally expanded and/or curved to extend along a path of a portion of the mandible to be replaced. As shown in FIGS. 1 and 2, the graft containment device 102 may be used with a fixation plate 120, which, in this embodiment, fixes the graft containment device 102 relative to remaining portions of the mandible while also maintaining a desired curve of the graft containment device 102. As shown in FIG. 2, the first and second connections 108, 110 at the various connection points 106 allow the graft containment device 102 to be easily adjusted to a predefined shape (e.g., curvature) of the fixation plate 120.

As described above, the graft containment device 102 includes a plurality of cage segments 104 connected to one another at various connection points 106. Each cage segment 104 may be formed of a mesh material, at least the connection points 106 having sufficient flexibility so that the graft containment device 102 may be bent and/or expanded as will be described in further detail below. The graft containment device 102 may be formed of, for example, any suitable polymer. The graft containment device 102 may be formed or a resorbable material, such as polycapralactone, or a nonresorbable material. Each cage segment 104 may include a plurality of pores 132 extending through the material thereof, the pores 132 shaped to promote vascularization of the bone while preventing graft material packed in the graft containment structure 104 from falling out of the device 102. The pores 132 may also be sized and shaped to receive a fixation elements therein. In one example, the pores 132 may be sized to receive a bone fixation screw having a 1.8 mm diameter. In another embodiment, the mesh material may be formed via a plurality of intersecting struts formed of a desired material, the struts intersecting to define the pores 132.

Figure 3:
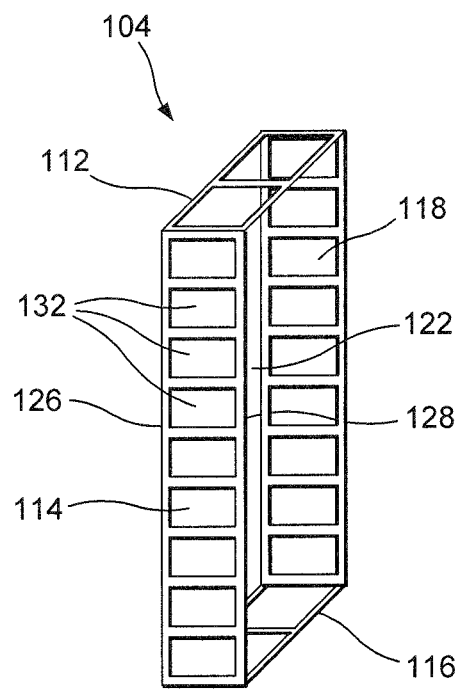
FIG. 3 shows a perspective view of a cage segment of the graft containment device of FIG. 1.

In this embodiment, as shown in FIG. 3, each cage segment 104 extends from a first end 126 to a second end 128 and may have a substantially rectangular profile including a first surface 112, a second surface 114, a third surface 116 and a fourth surface 118. The first and third surfaces 112, 116 may extend substantially perpendicular to the second and fourth surfaces 114, 118 with the first and third surfaces 112, 116 substantially opposing one another and the second and fourth surfaces 114, 118 substantially opposing one another to form a substantially rectangular structure. A channel 122 extends through the rectangular structure from the first end 126 to the second end 128. When the graft containment device 102 is in an operative position relative to the mandible, for example, the first surface 112 faces toward a superior direction while the third surface 116 faces toward an inferior direction and the second surface 114 faces toward a lingual direction while the fourth surface 118 faces toward a buccal direction. Adjacent cage segments 104 are connected to one another such that channels 122 of each of the cage segments 104 are aligned relative to one another. In other words, a first end 126 of one cage segment 104 is connected to a second end 128 of an immediately adjacent cage segment 104 so that the cage segments 104 form a graft containment device 102 which extends along a longitudinal axis L.

Figure 4:
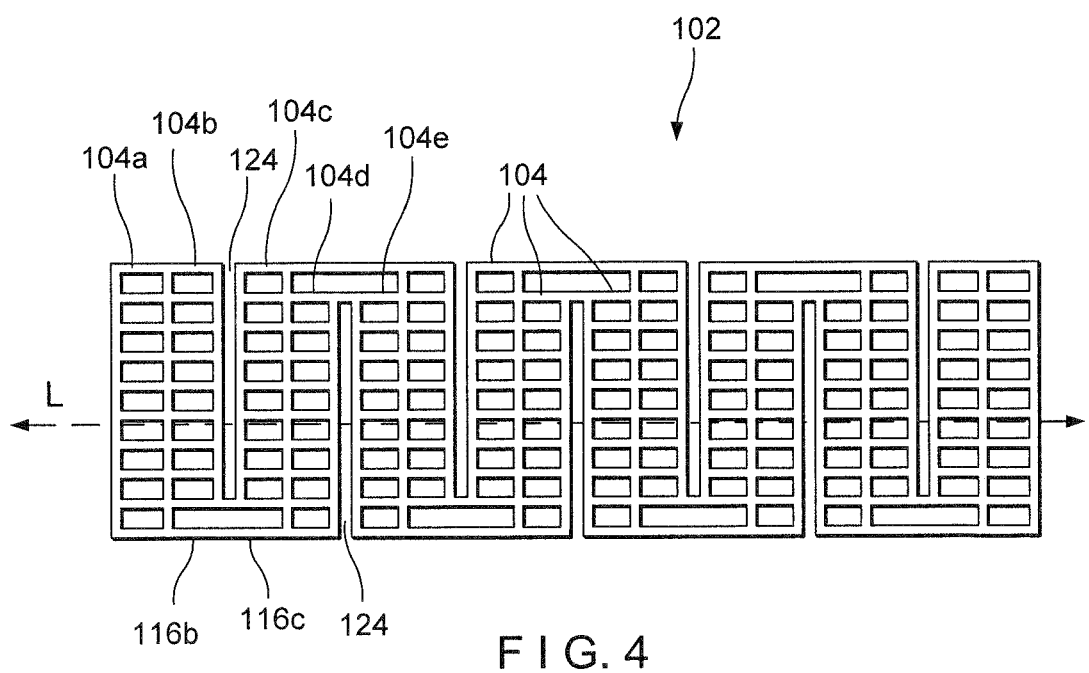
FIG. 4 shows a side view of the graft containment cage of the system of FIG. 1.
Figure 5:
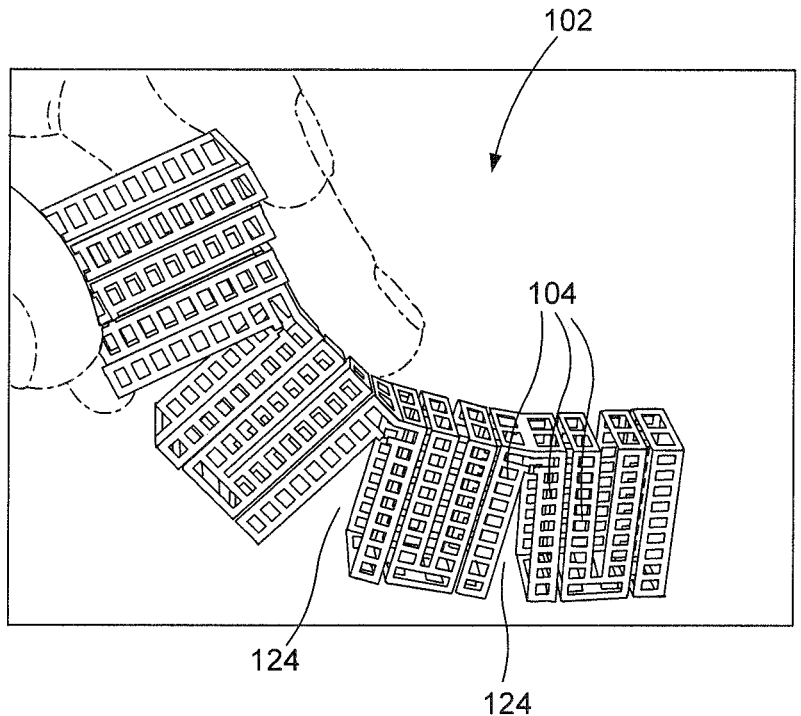
FIG. 5 shows a perspective view of a graft containment cage of the system of FIG. 1.
Figure 6:
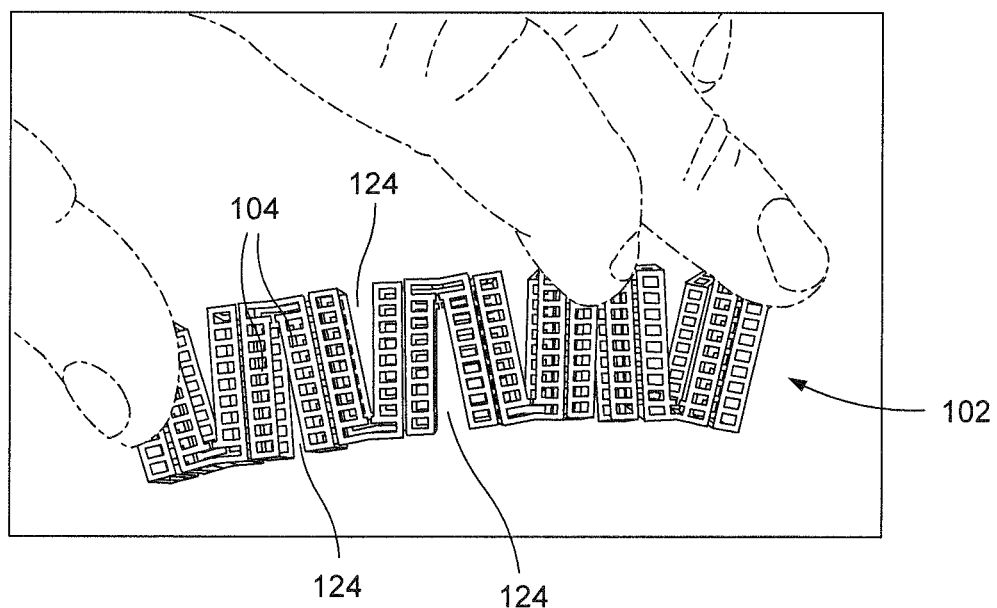
FIG. 6 shows a side view of the graft containment cage of the system of FIG. 1, in an extended configuration.
Figure 7:
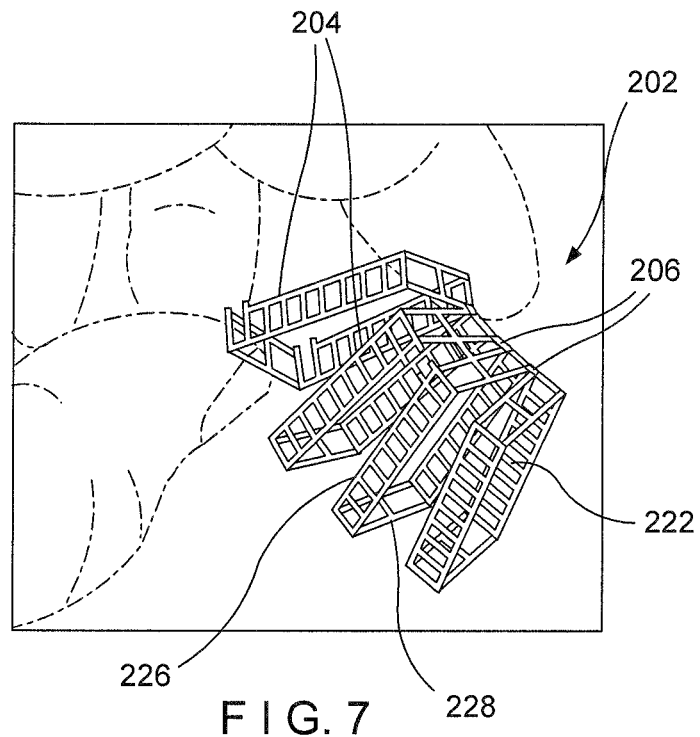
FIG. 7 shows a perspective view of a graft containment device according to another exemplary embodiment of the present disclosure.

Adjacent cage segments 104 may be connected to one another via either the first connection 108 or the second connection 110. The first connection 108 connects adjacent cage segments 104 along an entire edge of one of the surfaces 112-118 of the adjacent cage segments 104. For example, a first one of the cage segments 104a may be connected to a second one of the cage segments 104b via the first connection 108 along edges of fourth surfaces 118a, 118b of the first and second cage segments 104a, 104b, respectively. In other words, an edge at the second end 128 of the fourth surface 118a is connected to an edge at the first end 126 of the fourth surface 118b. The first connection 108 is formed such that, in a configuration to which the device 102 is biased, remaining surfaces 112-116 of the first and second cage segments 104a, 104b contact one another. The first connection 108 of this embodiment acts substantially as a hinged joint so that, when the first and second cage segments 104a, 104b are moved relative to one another, the first and second cage segments 104a, 104b "pivots" about the first connection 108. Thus, the first and second cage segments 104a, 104b may be moved relative to one another by pivoting about the first connection 108 so that first, second and third surfaces 112-116 may be separated from one another. In other words, in the biased configuration, the fourth surfaces 118a, 118b of the first and second cage segments 104a, 104b extend substantially in a single plane. The first and second cage segments 104a, 104b, however, may be moved relative to one another such that the fourth surface 118a of the first cage segments 104a is angled with respect to the fourth surface 118b of the second cage segments 104b about the first connection 108. The second connection 110 may connect two adjacent cage segments 104 via one of the surfaces 112-118 such that the two adjacent cage segments 104 may be distanced from one another to form a slot 124 therebetween, as shown in FIG. 4. For example, the second cage segment 104*b* may be connected to a third one of the cage segments 104*c* via the second connection 110 along third surfaces 116*b*, 116*c* of the second and third cage segments 104*b*, 104*c*, respectively. In one embodiment, third surfaces 116*b*, 116*c* of the second and third cage segments 104*b*, 104*c* may form one continuous surface, such that the slot 124 is formed between the second end 128 of the second cage segment 104*b* and the first end 126 of the third cage segment 104*c*, substantially transverse relative to the longitudinal axis L of the graft containment device 102. In the biased configuration, the third surfaces 116*b*, 116*c* may be substantially planar, extending along a single plane, and a size of the slot 124 (e.g., a distance between the second and third cage segments 104*b*, 104*c*) remains consistent along an entire length thereof. The slot 124, however, permits the graft containment device 102 extending therealong to be bent relative to the longitudinal axis L, as shown in FIG. 5, and/or extended along the longitudinal axis L, as shown in FIG. 6. When the graft containment device 102 is bent and/or extended, the third surfaces 116*b*, 116*c* may be bent or curved to increase a size of the slot 124.

In one embodiment, adjacent cage segments 104 are alternatingly connected to one another via the first and second connections 108, 110. For example, since the first cage segment 104*a* is connected to the second cage segment 104*b* via the first connection 108 and the second cage segment 104*b* is connected to the third cage segment 104*c* via the second connection 110, the third cage segment 104*c* will be connected to a fourth cage segment 104*d* via the first connection 108 and the fourth cage segment 104*d* is connected to a fifth cage segment 104*e* via the second connection. For example, an edge of at a second end 128 of a fourth surface 118*c* of the third cage segment 104*c* may also be connected to an edge at a first end 126 of a fourth surface 118*d* of the fourth cage segment 104*d*. In this embodiment, the first connections 108 may be formed at edges of the fourth surfaces 118 of adjacent cage segments 104 to achieve a bending trajectory particularly suited for treatment of the mandible (e.g., bending of the graft containment device 102 along a surface of the fixation plate fixation plate 120). It will be understood by those of skill in the art, however, that the first connections 108 may be formed along any of the surfaces 112, 118 to achieve a bending trajectory suited for other types of target bones to be treated.

A position of each of the second connections 110 may alternate along a length of the graft containment device so that alternating second connections 110 may extend on opposing sides of the longitudinal axis L. For example, whereas the second and third cage segments 104*b*, 104*c* are connected along the third surfaces 116*b*, 116*c* so that the slot 124 extends from the third surfaces 116*b*, 116*c* in the superior direction, the fourth cage segment 104*d* may be connected to the fifth cage segment 104*e* along first surfaces 112*d*, 112*e* of the fourth and fifth cage segments 104*d*, 104*e*, respectively, so that the slot 124 extends in an inferior direction therefrom. This alternating configuration of the second connections 110 permits both a bending of the graft containment device 102 and an extension of the graft containment device 102 along the longitudinal axis L.

The alternating pattern of connections 108, 110 described above may be continued along a length of the graft containment device. Although the exemplary embodiment shows and describes a specific pattern of connections 108, 110 at designated connection points 106, it will be understood by those of skill in the art that the connection points 106 and pattern of connections 108, 110 may be varied to achieve a desired bending/extension trajectory to suit the target bone being treated. In addition, although the exemplary embodiment shows and describes cage segments 104 having a substantially rectangular structure, it will be understood by those of skill in the art, that a cross-sectional profile of the cage segments 104 may be varied to correspond to a profile of the target bone being treated.

The graft containment device 102 may have any number of cage segments 104 and may extend along a desired length. In one embodiment, as shown, each cage segment 104 may have substantially similar proportions. It will be understood by those of skill in the art, however, that each cage segment 104 may be of varying sizes (e.g., length) and/or shape. The graft containment device 102 may be manufactured in a predetermined length, but may be trimmed, as desired, to fit the target space or gap of the target bone.

According to an exemplary method using the system 100, graft material may be packed into the channels 122 of the cage segments via ends of the graft containment device 102. Upon packing of the graft material, as desired, the graft containment device 102 may be bent and/or extended to fit the target space or gap of the bone being treated (e.g., mandible). If the graft containment device 102 is too long, however, the graft containment device 102 may be trimmed to a desired length. For example, the graft containment device 102 may be trimmed at a connection point 106 to remove a desired number of cage segments.

In one embodiment, the graft containment device 102 may be used with a fixation plate 120. In this case, the graft containment device 102 may be positioned against the fixation plate 120 such that the graft containment device 102 is bent/extended to adjust to the predefined shape of the fixation plate 120, as shown in FIG. 2. Once the graft containment device 102 has been adjusted, as desired, the fixation plate 120 may be fixed to the graft containment device 102 via fixation elements such as, for example, screws, which may be inserted through openings 130 of the fixation plate 120 and pores 132 of the cage segments 104. If so desired, additional graft material may be inserted into the graft containment device 102 via the slots 124 and any space between adjacent cage segments 104 resulting from the bending/extending of the graft containment device 102. Once the fixation plate 120 has been fixed to the graft containment device 102, the graft containment device 102 and fixation plate 120 assembly may be positioned in the target space/gap of the bone and fixed therein via the fixation plate 120, ends of which may overlap the separated portions of bone. The fixation plate 120 may be fixed to the bone via fixation elements inserted through openings 130 extending through portions of the fixation plate 120 overlapping the bone.

As described above, connection points and the types of connections between adjacent cage segments may be varied to form a graft containment device having a desired bending trajectory. According to another exemplary embodiment, as shown in FIGS. 8-11, a graft containment device 202 may be substantially similar to the graft containment device 102 described above, comprising a plurality of cage segments 204 connected to one another at connection points 206. Each cage segment 204 may be substantially similar to the cage segment 104, and may include, for example, a first surface 212, a second surface 214, a third surface 216 and a fourth surface 218 connected to one another to form a rectangular structure extending from a first end 226 to a second end 228 and including a channel 222 extending therethrough. Similarly to the graft containment device 102, these cage segments 204 are connected to one another along a longitudinal axis, a first end 226 of one cage segment 204 connected to a second end 228 of an adjacent cage segment 204. Rather than first and second connections 108, 110, however, the cage segments 204 are connected to one another along an edge 234 connecting two adjacent surfaces 212-218.

Figure 8:
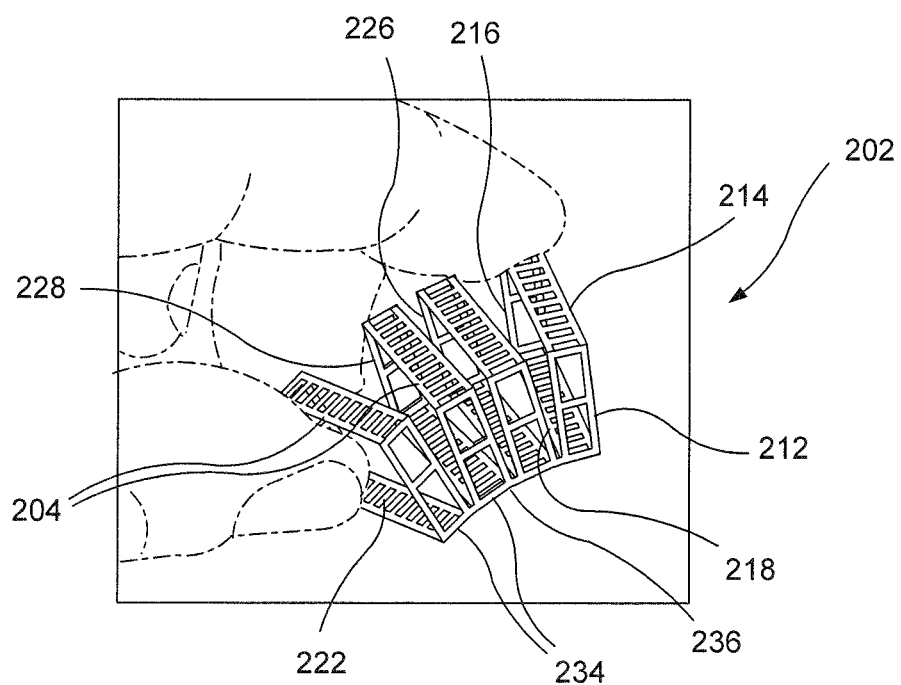
FIG. 8 shows another perspective view of the graft containment device of FIG. 6.
Figure 9:
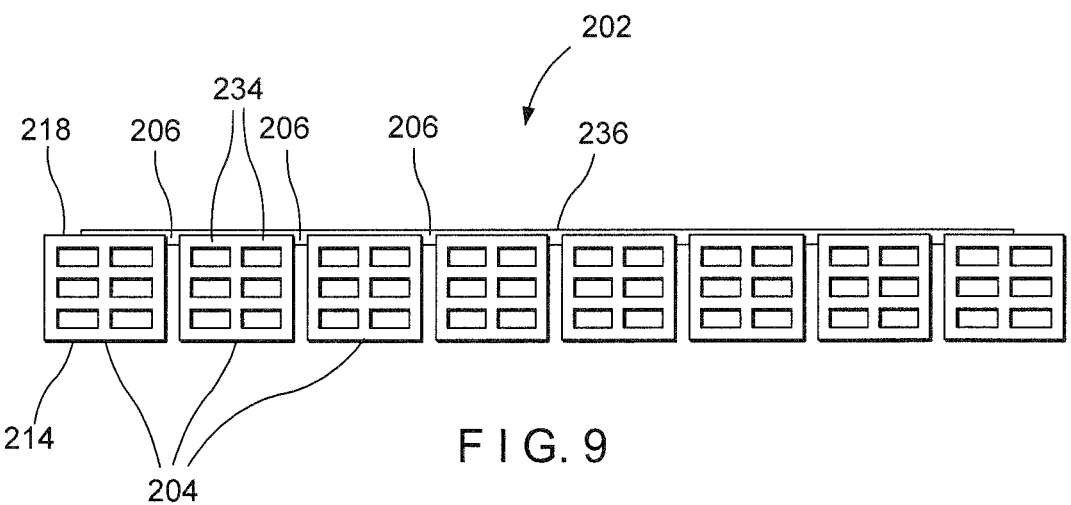
FIG. 9 shows a top plan view of the graft containment device of FIG. 6.
Figure 10:
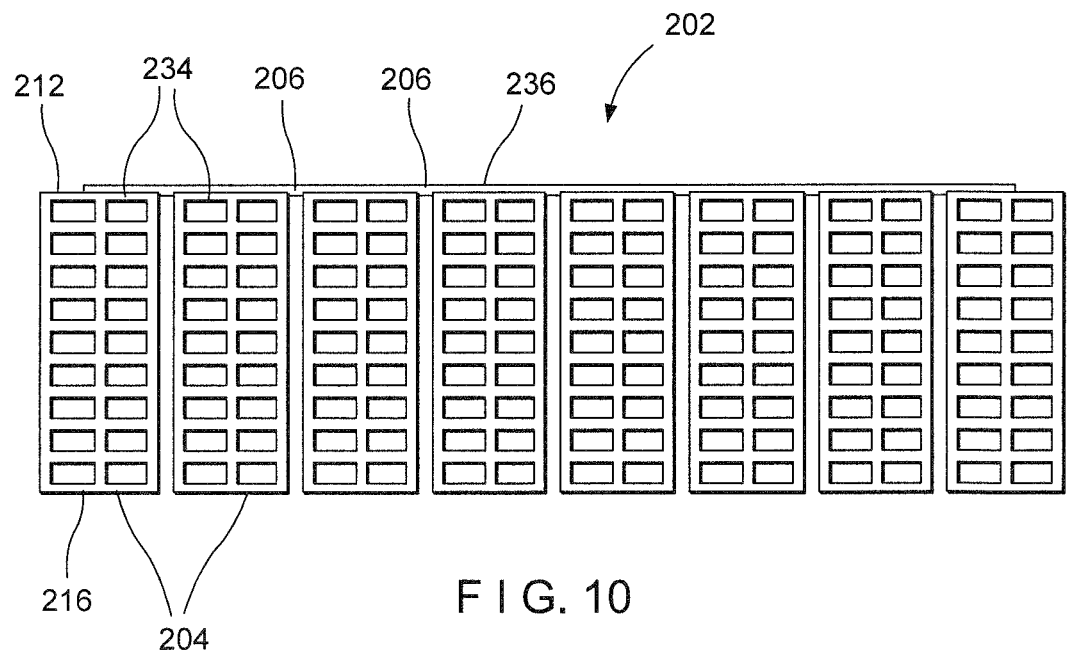
FIG. 10 shows a side view of the graft containment device of FIG. 6.
Figure 11:
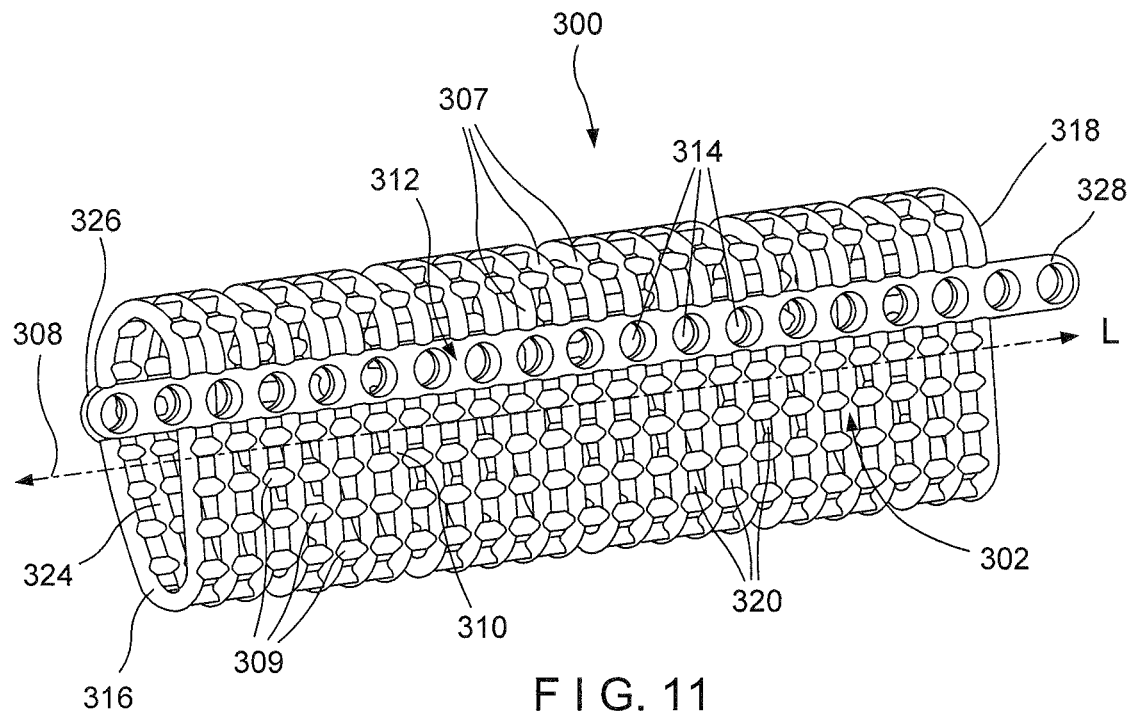
FIG. 11 shows a perspective view of a device according to another exemplary embodiment of the present disclosure.
Figure 12:
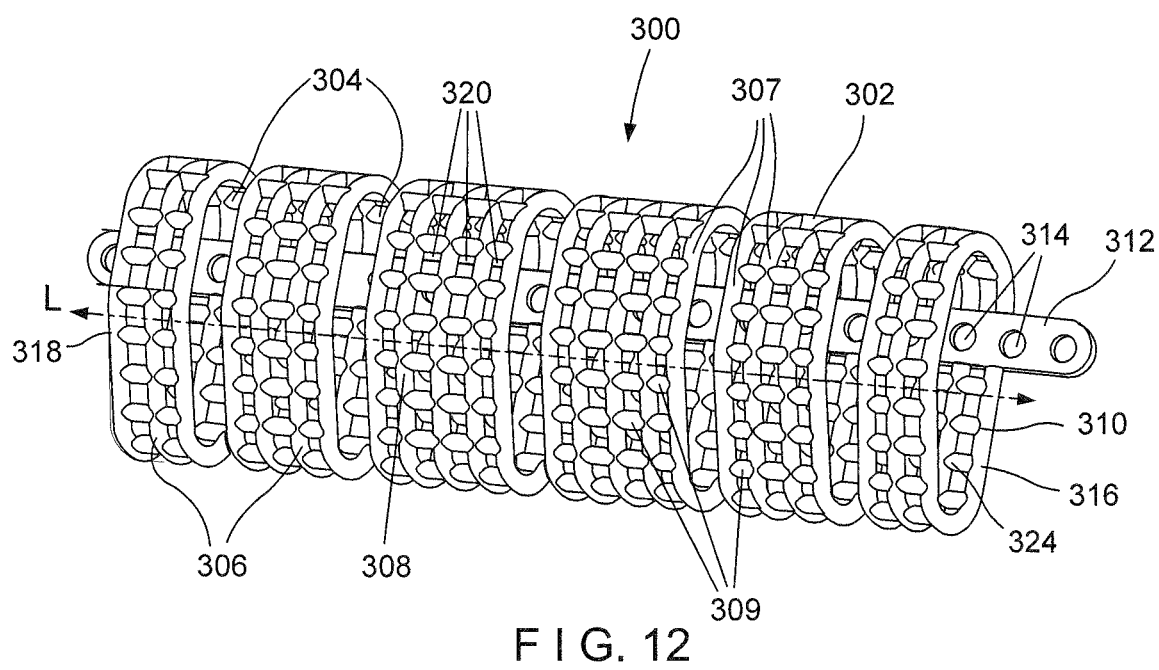
FIG. 12 shows another perspective view of the device of FIG. 11.

In the embodiment shown, for example, the cage segments 204 are connected along an edge 234 along which the first and fourth surfaces 212, 218 meet via a connecting edge 236. The connecting edge 236 may be configured as, for example, a strut extending between the cage segments 204. In a biased configuration, the connecting edge 236 extends along a substantially straight line. When adjacent cage segments 204 are moved relative to one another, however, the connecting edge 236 may be bent or curved so that portions of adjacent cage segments 204 are separated from one another. In one embodiment, as shown in FIGS. 8-9, the second end 228 of one cage segment 204 may be in contact with the first end 226 of an adjacent cage segment 204, in the biased configuration. In another embodiment, as shown in FIGS. 10-11, the first end 226 of a cage segment 204 is separated from the second end of the adjacent cage segment 204 so that a space exists therebetween. It will be understood by those of skill in the art, that the graft containment device 202 may be used in a manner substantially similar to the graft containment device 102. Like the graft containment device 102, the graft containment device 202 may also be used in conjunction with a fixation plate.

Although the exemplary embodiments show and describe graft containment devices 102, 202 having specific connection points 106, 206 with specific connection types (e.g., connection 108, 110 and connecting edge 236), it will be understood by those of skill in the art that the present disclosure includes graft containment devices having any of a variety of connection points with any of a variety of combinations of connection types. It will be understood by those of skill in the art that connections between adjacent cage segments may be selected to obtain a desired trajectory of movement of the graft containment device.

As shown in FIGS. 11-14, a graft containment device 300 according to another exemplary embodiment of the present disclosure may be substantially similar to the graft containment devices 102, 202 described above, comprising a body 302 defined via cage segments 306. The cage segments 306, however, as will be described in further detail below, are connected to one another via a continuous surface extending along sides of the segments 306 which, when in an operative position, may face toward a lingual direction. In addition, the graft containment device 300 may be formed to include a fixation tab 312 so that a fixation plate is not required for fixing the graft containment device 300 relative to the bone.

The body 302 extends along a longitudinal axis L and includes a channel 324 extending therethrough along the longitudinal axis L for receiving graft material. A plurality of slots 304 extend laterally into the body 302 at an angle relative to the longitudinal axis L to define cage segments 306 separated from one another by the slots 304. For example, in this embodiment, the device 300 includes a lattice formed by a series of generally circumferential members 307 interconnected by a series of longitudinal members 309. The slots 304 of this embodiment are formed as areas in which adjacent ones of the circumferential members 307 are not coupled to each other by longitudinal members about a portion of the circumference of the device 300. For example, in the embodiment of FIG. 11, the slots 304 are formed as areas free of longitudinal members 309 so that continuous longitudinal members 309 extend only along one planar face of the body 302, as described below. In particular, the slots 304 extend into the body 302 along a first side 308 of the body 302 which, when the device 300 is in an operative position within a mandible, faces toward a lingual direction, so that a second side 310 of the body 302 opposite the first side 308 which, in the operative position, faces toward a buccal direction, includes a continuous surface with each adjacent pair of circumferential members 307 connected to each other by multiple longitudinal members 309. The slots 304 (e.g., area of the body 302 free of longitudinal members 309) along the first side 308 permit a lateral bending of the body 302.

When the graft containment device 300 is positioned within a target space of a bone such as the mandible, the first side 308 may face in a lingual direction while the second side 310 may face toward a buccal direction. The graft containment device 300 may be bent from a substantially straight first configuration toward a curved second configuration, in which the cage segments 306 are moved toward one another to reduce the size of the spaces between adjacent cage segments 306 (i.e., by drawing edges of adjacent cage segments toward one another at the slots 304) so that a curved path of the graft containment device 300 substantially corresponds to a curve of a portion of the mandible to be replaced. The graft containment device 300 may further include a fixation tab 312 integrated with the body 302 for fixing the body 302 to surrounding portions of bone. The fixation tab 312 includes a plurality openings 314 extending along a length thereof for receiving bone fixation elements therein. The fixation tab 312 may extend beyond ends of the body 302 so that, when the body 302 is positioned in the space of the target bone to be replaced, ends of the fixation tab 312 extend over remaining portions of bone at either end or both ends of the target portion of bone to be replaced to so that graft containment device 300 may be fixed to the remaining bone via the fixation tab 312. In another embodiment, the graft containment device 300 may also be used with a fixation plate, which may be fixed to the device via bone fixation elements inserted through pores 320 of the body 302, as will be described in further detail below.

As described above, the body 302 of this embodiment is formed as a mesh (a lattice of circumferential and longitudinal members 307, 309, respectively) of material having sufficient flexibility so that the graft containment device 302 may be bent, as will be described in further detail below. The body 302 may be formed of, for example, any suitable biocompatible polymer. The body 302 may be formed of a resorbable polymer such as polycapralactone, or a nonresorbable material. The circumferential and longitudinal members 307, 309, respectively, of the body 302 are spaced from one another by distances selected to form a plurality of pores 320 sized to promote vascularization of the bone while preventing graft material packed in the body 302 from falling out of the body 302. For example, pores 320 having a size greater than 0.3 mm may promote vascularization of the bone. In an alternate embodiment, the body 302 may be formed of a mesh material without discrete circumferential members 307 and longitudinal members 309 including pores 320 sized similarly to those formed in the device 300 of FIG. 1. The pores 320 may also be sized and shaped to receive bone fixation elements therethrough. In one example, a selected number of the pores 320 may have a size of approximately 1.8 mm, which, as will be understood by those of skill in the art, may receive 2.4 mm bone fixation screws. Thus, in cases in which the graft containment device is used with a fixation plate, bone fixation elements may be inserted through openings of the fixation plate and through pores of the body 302 to fix the fixation plate relative to the graft containment device 300.

The body 302 of the graft containment device 300 extends along the longitudinal axis L from a first end 316 to a second end 318 and includes the channel 324 extending therethrough along the longitudinal axis L. The plurality of slots 304 extend laterally into the first side 308 of the body 302 so that the slots 304 are in communication with the channel 324. The slots 304 extend into the body 302 at an angle relative to the longitudinal axis L. In one embodiment, the slots 304 may extend into the body 302 substantially perpendicularly to the longitudinal axis L. As described above, the slots 304 extend along the first side 308 of the body 302 so that the second side 310 of the body 302 opposite the first side 308 includes a continuous surface. The slots 304 extending into the body 302 to define the cage segments 306. In one embodiment, the slots 304 may be equidistantly spaced from one another so that the resulting cage segments 306 are uniform in length. In another embodiment, a distance between adjacent slots 304 may vary so that the cage segments 306 may vary in length along a length of the body 302. Thus, lengths of each of the cage segments 306 may vary depending on a desired stability and/or desired increased curvature of the body 302. For example, shorter cage segments 306 permit greater bending along a corresponding portion of the graft containment device 300 while longer cage segments 306 may have limited bending but provide greater stability.

Figure 13:
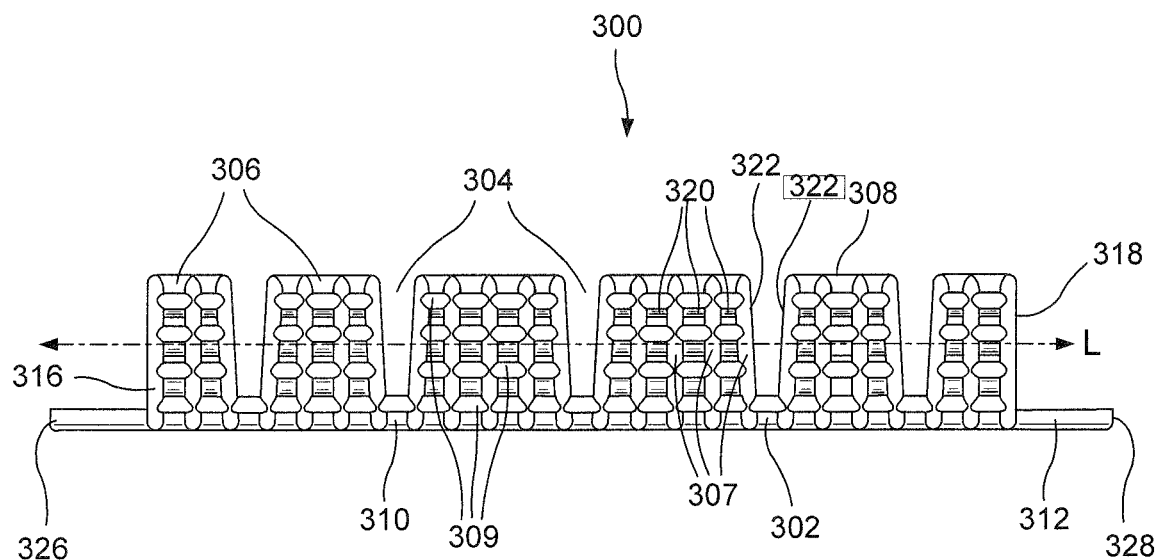
FIG. 13 shows a top plan view of the device of FIG. 11.

It will be understood by those of skill in the art that a size of the slots 304 between adjacent cage segments 306 determines a degree of permitted bending between adjacent cage segments 306. To permit increased bending without substantially increasing the size of the slots 304, the slots 304 may be angulated relative to an axis perpendicular to the longitudinal axis L, as shown in FIG. 13, by angles of approximately +/− 5 degrees. Each of the slots 304 may taper from the first side 308 of the body 302 toward the second side 310 of the body 302 so that a size (e.g., a distance between adjacent cage segments 306) of the slot 304 decreases as the slot 304 extends toward the second side 310. In other words, edges 322 of each of the cage segments 306 are angled relative to an axis perpendicular to the longitudinal axis L so that each cage segment 306 tapers from the second surface 310 toward the first surface 308. When the edges 322 of adjacent cage segments 306 contact one another, the adjacent cage segments 306 cannot be bent any further relative to one another. Thus, the angles of the slots 304/edges 322 define a maximum permitted bending of the graft containment device 300. In an exemplary embodiment, adjacent cage segments 306 may be separated from one another by a distance of between approximately 1.8 mm (e.g., the size of one pore with no angulation of the edges 322) to approximately 8.6 mm (e.g., the size of three pores including angulation of the edges 322). Although the slots 304 are shown as consistently sized along a length of the body 302, it will be understood by those of skill in the art that the slots 304 may vary in size along the length of the body 302 to achieve a desired bending configuration of the body 302.

Figure 14:
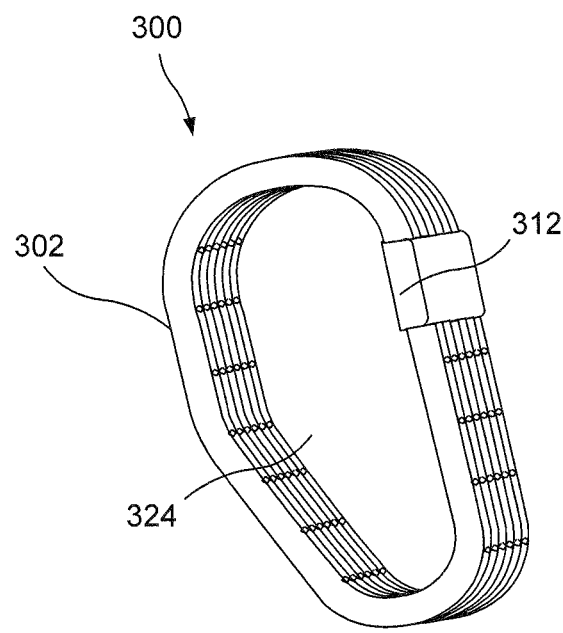
FIG. 14 shows yet another perspective view of the device of FIG. 11.

In one exemplary embodiment, the graft containment device 302 is sized and shaped to be positioned between two separated portions of a target bone. As shown in FIG. 14, a lateral cross-section of the body 302 may substantially match an outer profile of a target portion of bone which formerly occupied the space to be occupied by the device 300. Where the target bone is the mandible, the cross-section of the body 302 may substantially correspond to a cross-section of a mandible. The cross-section may provide for future bone bulk in relevant areas while minimizing pressure on soft tissue. For example, the first surface 308, which, when the graft containment device 300 is positioned in the target space of the mandible faces a lingual direction, may taper toward an inferior direction. This permits bulk along a superior portion of the graft containment device 300.

The fixation tab 312 may be integrally formed with the body 302 and may extend longitudinally along the second surface 310 of the body 302. In one embodiment, the fixation tab 312 may extend substantially parallel to the longitudinal axis L. The fixation tab 312 extends from a first end 326 to a second end 328, the first end 326 extending beyond the first end 316 of the body 302 and the second end 328 extending beyond the second end 318 of the body 302 so that, when the body 302 is positioned within the target space of the bone, the first and second ends 326, 328 of the fixation tab 312 may extend over separated portions of the bone which are being bridged by the graft containment device 300. The fixation tab 312 includes a plurality of openings 314 extending therethrough, along a length thereof. Each of the openings 314 are sized and shaped to receive a bone fixation element therein. Thus, bone fixation elements may be inserted through openings 314 along the first and second ends 326, 328 of the fixation tab 312 to fix the graft containment device 300 relative to the bone.

The graft containment device 300 may have any number of cage segments 306 and may extend along any desired length. As described above, each cage segment 306 may have substantially similar proportions or may be of varying sizes (e.g., length) to attain a desired stability and/or bendability of the graft containment device 300 that is uniform or that varies in a desired manner along a length of the device 300. The graft containment device 300 may be manufactured in a predetermined length, but may be trimmed, as desired, to fit the target space or gap of the target bone. In particular, a length of the graft containment device 300 may be modified by cutting the body 302 between adjacent cage segments 306. Since the openings 314 may extend along an entire length of the fixation tab 312, the fixation tab 312 may also be trimmed so that an end thereof always extends beyond a cut end of the body 302. According to an exemplary method using the graft containment device 300, graft material is packed into the channel 324 of the body 302 via the first and second ends 316, 318 of the body 302 and/or via the slots 304. Upon packing of the graft material, as desired, the body 302 may be bent relative to the longitudinal axis L to fit the target space or gap of the bone being treated (e.g., mandible). If the graft containment device 300 is too long, however, the graft containment device 300 may be trimmed to a desired length. For example, the graft containment device 300 may be trimmed at a point between adjacent cage segments 306 so that a desired number of cage segments 306 may be removed. Additionally, the graft containment device 300 may be trimmed to increase a size of one or more slots 304 of the body 302 to increase a bending curvature of the body 302. For example, portions of circumferential and/or longitudinal members 307, 309 adjacent to the edges 322 defining the slots 304 may be cut/removed to increase the size of the slots 304.

Once the body 302 has been bent, as desired, the body 302 may be positioned in the target space or gap so that first and second ends 326, 328 of the fixation tab 312 extend over separated portions of the bone, which are being bridged by the graft containment device 300. Bone fixation elements are inserted into openings 314 along the first and second ends 326, 328 to fix the graft containment device 300 to the bone. Although not shown, it will be understood by those of skill in the art that the graft containment device 300 may be utilized in conjunction with a fixation plate. In cases in which a fixation plate is desired to be used, the graft containment device 300 may be positioned against the fixation plate such that the graft containment device 300 is bent to adjust to the predefined shape of the fixation plate. Once the graft containment device 300 has been adjusted, as desired, the fixation plate may be fixed to the graft containment device 300 via fixation elements such as, for example, screws, which may be inserted through openings of the fixation plate and pores 320 of the mesh body 302.

It will be understood by those of skill in the art that modifications and variations may be made in the structure and methodology of the present invention, without departing from the spirit or the scope of the invention. Thus, it is intended that the present invention cover the modifications and variations of this invention, provided that they come within the scope of the appended claims and their equivalents.

What is claimed is:

1. A bone graft containment device, comprising a plurality of cage segments connected to one another along a longitudinal axis, adjacent ones of each of a first portion of the cage segments being connected to one another via a first connection which permits movement of the connected cage segments of the first portion of the cage segments relative to one another so that the bone graft containment device is deformable to a desired configuration for placement within a target space of a bone, each cage segment extending along from a first end to a second end and including a channel extending therethrough so that channels of the plurality of cage segments, in an initial configuration, are aligned along the longitudinal axis, the channels configured to be packed with a bone graft material.

2. The device of claim 1, wherein adjacent ones of a second portion of the cage segments are connected to one another via a second connection in which a slot extends between the connected cage segments of the second portion of cage segments so that a remaining, non-connected portions of the connected cage segments of the second portion of cage segments are separated from one another.

3. The device of claim 2, wherein the adjacent cage segments connected by the second connection are connected to one another via a continuous surface extending therebetween.

4. The device of claim 3, wherein, in the initial configuration, the continuous surface is substantially planar.

5. The device of claim 1, wherein the first connection connects a portion of an edge of one of the cage segments with a portion of the edge of the adjacent cage segment.

6. The device of claim 5, wherein, in the initial configuration, non-connected portions of the adjacent cage segments connected by the first connection are in contact with one another.

7. The device of claim 1, wherein a cross-sectional area of the cage segments correspond to a cross-sectional area of the bone.

8. The device of claim 1, wherein each cage segment is configured as a substantially rectangular structure.

9. The device of claim 1, wherein each cage segment is formed of a mesh material including a plurality of pores extending therethrough.

10. The device of claim 1, wherein each cage segment includes a plurality of pores, the pores sized and shaped to prevent graft material packed in the graft containment device from falling out of the graft containment device.

11. The device of claim 10, wherein at least one of the pores is sized and shaped to receive a portion of a bone fixation element.

12. The device of claim 11, wherein the bone fixation element is a screw.

13. A bone graft containment system, comprising:
a bone graft containment device comprising a first cage segment extending from a first end to a second end and including a first channel extending therethrough, a second cage segment extending from a first end to a second end and including a second channel extending therethrough, the first end of the second cage segment connected to the second end of the first cage segment via first connection so that, when in an initial configuration, the first and second channels are aligned along a longitudinal axis, the first and second cage segments being movable relative to one another to a desired configuration for placement in a target space of a bone, the first and second channels configured to be packed with a bone graft material and a first slot extending between the first and second cage segments to define a space therebetween; and
a bone plate configured to be coupled to the bone graft containment device, movement of the first and second cage segments relative to one another permitting the bone graft containment device to conform to a shape of the bone plate.

14. The system of claim 13, further including a third cage segment connected to the second cage segment via a second connection wherein the second connection includes a continuous surface extending between portions of the third and second cage segments, wherein the third cage segment extends from a first end to a second end and includes a third channel extending therethrough, the first end of the third cage segment movably connected to the second end of the second cage segment via the second connection so that the third channel is aligned with the second channel along the longitudinal axis, in the initial configuration.

15. The system of claim 14, wherein the continuous surface is substantially planar in the biased configuration.

16. The system of claim 14, wherein the first connection includes a strut extending between the first cage and the second cage.

17. The system of claim 14, further comprising a second slot extending between the second and third cage segments to define a space therebetween.

18. The system of claim 17, wherein the first and second slots are open to an exterior of the device on opposing sides of the longitudinal axis.

19. The system of claim 13, wherein each of the first and second cage segments includes a plurality of pores, the pores sized and shaped to prevent graft material packed in the graft containment device from falling out of the graft containment device and wherein the bone plate is sized so that, when the bone graft containment device is in a desired position between separated portions of bone to be treated, the bone plate overlaps the separated portions of bone for fixation to the separated portions of the bone.

20. The system of claim 19, wherein the bone plate includes a plurality of bone fixation element receiving holes extending therethrough, the bone fixation element receiving holes being configured so that, when the bone plate is positioned on the bone graft containment device as desired, each bone fixation element inserted through a respective one of the bone fixation element receiving holes extends into a corresponding one of the pores to lock the bone plate to the bone graft containment device.

* * * * *